(12) United States Patent
Anderson et al.

(10) Patent No.: US 10,155,119 B2
(45) Date of Patent: *Dec. 18, 2018

(54) EXTRA-CARDIOVASCULAR PACING USING HIGH-VOLTAGE THERAPY CIRCUITRY OF AN IMPLANTABLE CARDIOVERTER DEFIBRILLATOR

(71) Applicant: Medtronic, Inc., Minneapolis, MN (US)

(72) Inventors: David A. Anderson, Stanchfield, MN (US); Mark T. Marshall, Forest Lake, MN (US); Vladimir P. Nikolski, Blaine, MN (US); Robert T. Sawchuk, Roseville, MN (US); Amy E. Thompson-Nauman, Ham Lake, MN (US); John D. Wahlstrand, Shoreview, MN (US); Gregory A. Younker, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 4 days.

This patent is subject to a terminal disclaimer.

(21) Appl. No.: 15/367,777

(22) Filed: Dec. 2, 2016

(65) Prior Publication Data

US 2017/0157414 A1 Jun. 8, 2017

Related U.S. Application Data

(60) Provisional application No. 62/262,499, filed on Dec. 3, 2015.

(51) Int. Cl.
*A61N 1/39* (2006.01)
*A61N 1/362* (2006.01)
(Continued)

(52) U.S. Cl.
CPC ......... *A61N 1/3962* (2013.01); *A61N 1/3621* (2013.01); *A61N 1/371* (2013.01);
(Continued)

(58) Field of Classification Search
CPC .... A61N 1/3962; A61N 1/3621; A61N 1/371; A61N 1/3758; A61N 1/3987
See application file for complete search history.

(56) References Cited

U.S. PATENT DOCUMENTS

| 5,184,616 A | 2/1993 | Weiss |
| 5,215,083 A | 6/1993 | Drane et al. |

(Continued)

FOREIGN PATENT DOCUMENTS

| EP | 2376193 B1 | 3/2014 |
| WO | 9316757 A1 | 9/1993 |

(Continued)

OTHER PUBLICATIONS

Thompson-Nauman et al., "Extra-Cardiovascular Cardiac Pacing System", U.S. Appl. No. 14/957,651, filed Dec. 3, 2015, 65 pages.

(Continued)

*Primary Examiner* — Joseph Dietrich

(57) ABSTRACT

This disclosure is directed to techniques for delivering cardiac pacing pulses to a patient's heart by a cardiac system, such as an extra-cardiovascular ICD system. An ICD operating according to the techniques disclosed herein delivers cardiac pacing pulses using high-voltage therapy circuitry typically configured for delivering high-voltage cardioversion/defibrillation shocks. The ICD delivers the high-voltage pacing therapy via extra-cardiovascular electrodes, such as one or more extra-cardiovascular electrodes carried by a medical electrical lead extending from the ICD and/or the housing of the ICD.

26 Claims, 12 Drawing Sheets

(51) Int. Cl.
*A61N 1/37* (2006.01)
*A61N 1/375* (2006.01)
*A61N 1/05* (2006.01)

(52) U.S. Cl.
CPC ......... *A61N 1/3706* (2013.01); *A61N 1/3712* (2013.01); *A61N 1/3758* (2013.01); *A61N 1/3925* (2013.01); *A61N 1/3987* (2013.01); *A61N 1/0587* (2013.01)

(56) References Cited

U.S. PATENT DOCUMENTS

| | | | |
|---|---|---|---|
| 5,824,018 A | 10/1998 | Dreher et al. | |
| 6,778,860 B2 | 8/2004 | Ostroff et al. | |
| 6,856,835 B2 | 2/2005 | Bardy et al. | |
| 6,865,417 B2 | 3/2005 | Rissman et al. | |
| 6,952,608 B2 | 10/2005 | Ostroff | |
| 6,952,610 B2 | 10/2005 | Ostroff et al. | |
| 6,954,670 B2 | 10/2005 | Ostroff | |
| 7,092,754 B2 | 8/2006 | Bardy et al. | |
| 7,146,212 B2 | 12/2006 | Bardy et al. | |
| 7,184,833 B2 | 2/2007 | Ganion et al. | |
| 7,389,139 B2 | 6/2008 | Ostroff | |
| 7,392,081 B2 | 6/2008 | Wagner et al. | |
| 7,471,983 B2 | 12/2008 | Voegele et al. | |
| 7,502,645 B2 | 3/2009 | Ostroff et al. | |
| 7,522,957 B2 | 4/2009 | Ostoff | |
| 7,751,885 B2 | 7/2010 | Bardy et al. | |
| 7,761,150 B2 | 7/2010 | Ghanem et al. | |
| 8,036,742 B2 | 10/2011 | Sullivan et al. | |
| 8,155,740 B2 | 4/2012 | Wanasek | |
| 8,195,291 B2 | 6/2012 | Norton et al. | |
| 8,359,094 B2 | 1/2013 | Bonner et al. | |
| 8,412,320 B2 | 4/2013 | Ostroff et al. | |
| 8,452,399 B2 | 5/2013 | Wanasek | |
| 8,758,365 B2 | 6/2014 | Bonner et al. | |
| 8,914,105 B2 | 12/2014 | Wanasek et al. | |
| 2008/0183230 A1 | 7/2008 | Kemmetmueller et al. | |
| 2008/0275531 A1 | 11/2008 | Bulkes et al. | |
| 2009/0210021 A1 | 8/2009 | Ostroff | |
| 2012/0197330 A1 | 8/2012 | Crutchfield et al. | |
| 2014/0330328 A1 | 11/2014 | Christie et al. | |
| 2015/0300375 A1 | 10/2015 | Begon et al. | |
| 2015/0306410 A1 | 10/2015 | Marshall et al. | |
| 2016/0158567 A1 | 6/2016 | Marshall et al. | |

FOREIGN PATENT DOCUMENTS

| | | |
|---|---|---|
| WO | 9958192 A1 | 11/1999 |
| WO | 2006115940 A1 | 11/2006 |
| WO | 2010088355 A1 | 8/2010 |
| WO | 2015164442 A1 | 10/2015 |
| WO | 2015164473 A1 | 10/2015 |

OTHER PUBLICATIONS (PCT/US2016/064646) PCT Notification of Transmittal of the International Search Report and the Written Opinion of the International Searching Authority, dated Mar. 17, 2017, 10 pages.

(PCT/US2016/064582) PCT Notification of Transmittal of the International Search Report and the Written Opinion of the International Searching Authority, dated Mar. 17, 2017, 14 pages.

EXTRA-CARDIOVASCULAR PACING USING HIGH-VOLTAGE THERAPY CIRCUITRY OF AN IMPLANTABLE CARDIOVERTER DEFIBRILLATOR

REFERENCE TO RELATED APPLICATION

This application claims the benefit of U.S. Patent Application No. 62/262,499, filed provisionally on Dec. 3, 2015, the content of which is incorporated herein by reference in its entirety.

TECHNICAL FIELD

The disclosure relates generally to an extra-cardiovascular implantable cardiac system, device and method for delivering cardiac pacing pulses using high-voltage therapy circuit and extra-cardiovascular electrodes.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation.

SUMMARY

In general, the disclosure is directed to techniques for delivering cardiac pacing pulses to a patient's heart by a cardiac system, such as an extra-cardiovascular ICD system. An ICD operating according to the techniques disclosed herein delivers cardiac pacing pulses using high-voltage therapy circuitry typically configured for delivering high-voltage cardioversion/defibrillation shocks. The ICD delivers the high-voltage pacing therapy via extra-cardiovascular electrodes, such as one or more extra-cardiovascular electrodes carried by a medical electrical lead extending from the ICD and/or the housing of the ICD.

In one example, the disclosure provides an extra-cardiovascular implantable cardioverter defibrillator (ICD) including a high voltage therapy module and a control module coupled to the high voltage therapy module. The high voltage therapy module includes a high voltage capacitor, a high voltage charging circuit configured to charge the high voltage capacitor, switching circuitry configured to couple the high voltage capacitor across a pacing load that includes extra-cardiovascular electrodes, and a variable shunt resistance in parallel with the pacing load. The control module is configured to apply an electrical current to enable the switching circuitry; set the variable shunt resistance to a value that keeps the switching circuitry enabled during delivery one or more pacing pulses to the pacing load; and control the high voltage therapy module to generate and deliver the one or more extra-cardiovascular pacing pulses via the extra-cardiovascular electrodes.

In another example, the disclosure provides an extra-cardiovascular implantable cardioverter defibrillator (ICD) including a high voltage therapy module and a control module coupled to the high voltage therapy module. The high voltage therapy module includes a high voltage capacitor; a high voltage charging circuit configured to charge the high voltage capacitor; switching circuitry configured to couple the high voltage capacitor across a pacing load that includes extra-cardiovascular electrodes; and a shunt resistance in parallel with the pacing load. The value of the shunt resistance is selected to keep the switching circuitry enabled during delivery of one or more pacing pulses to the pacing load over desired range of pacing amplitudes and pacing load impedances. The control module is configured to apply an electrical current to enable the switching circuitry and control the high voltage therapy module to generate and deliver the one or more extra-cardiovascular pacing pulses via the extra-cardiovascular electrodes.

In another example, the disclosure provides an extra-cardiovascular implantable cardioverter defibrillator (ICD) including a high voltage therapy module and a control module coupled to the high voltage therapy module. The high voltage therapy module includes a high voltage capacitor; a high voltage charging circuit configured to charge the high voltage capacitor; switching circuitry configured to couple the high voltage capacitor across a pacing load that includes extra-cardiovascular electrodes; and a shunt resistance in parallel with the pacing load. The control module is configured to apply an electrical current to enable the switching circuitry; select a pacing pulse voltage amplitude to have a minimum pacing pulse voltage amplitude to keep the switching circuitry enabled during delivery of one or more pacing pulses to the pacing load; and control the high voltage therapy module to generate and deliver the one or more extra-cardiovascular pacing pulses via the extra-cardiovascular electrodes.

In another example, the disclosure provides a method performed by an extra-cardiovascular implantable cardioverter defibrillator (ICD) having a high voltage therapy module. The method includes applying, by a control module of the ICD, an electrical current to enable switching circuitry configured to couple a high voltage capacitor of the therapy module across a pacing load that includes extra-cardiovascular electrodes; setting, by the control module of the ICD, a variable shunt resistance of the therapy module, the variable shunt resistance being in parallel with the pacing load, to a value that keeps the switching circuitry enabled during delivery of one or more pacing pulses to the pacing load; controlling the high voltage therapy module to charge a high voltage capacitor of the therapy module; and configuring the switching circuitry to discharge the high voltage capacitor across the pacing load to deliver the one or more pacing pulses via the extra-cardiovascular electrodes.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for delivering cardiac pacing pulses using high-voltage therapy circuitry and implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for automatically configuring an ICD pacing output configuration using extra-cardiovascular electrodes.

Figure 1A:
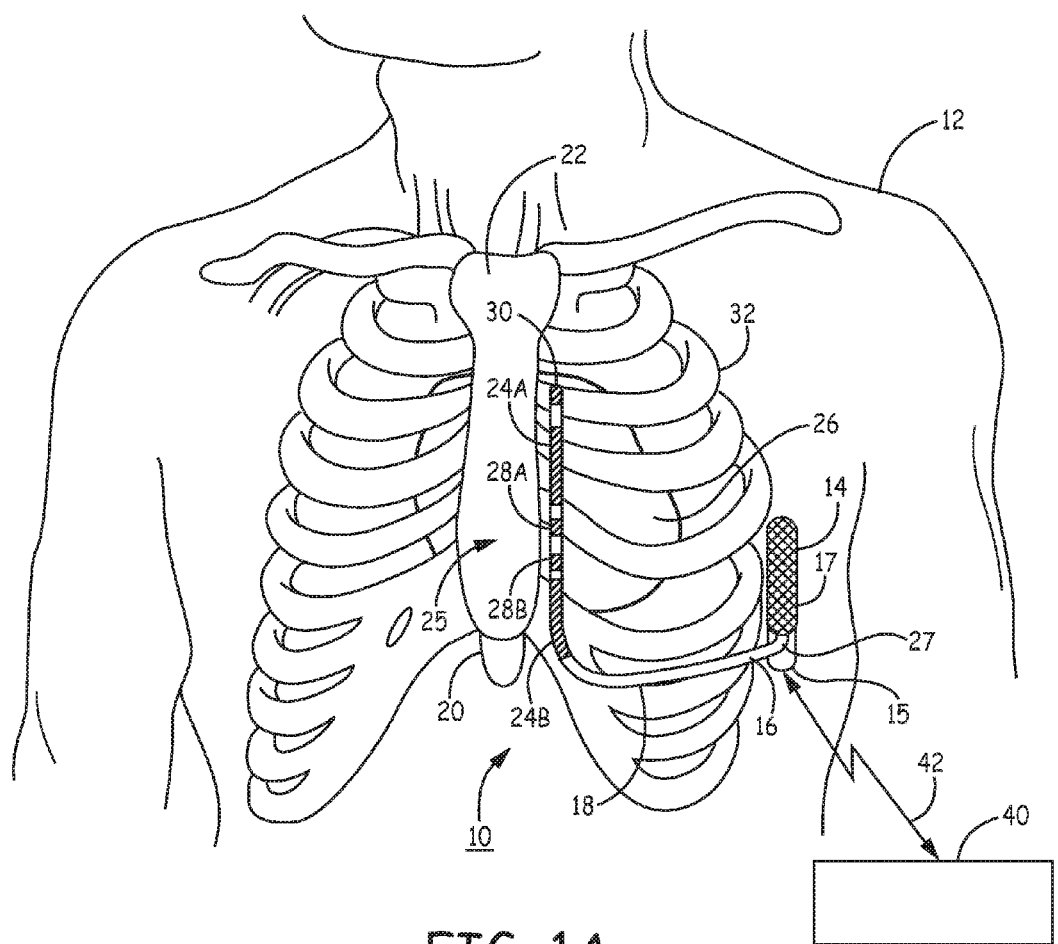
FIGS. 1A and 1B are conceptual diagrams of an extra-cardiovascular ICD system according to one example.
Figure 1B:
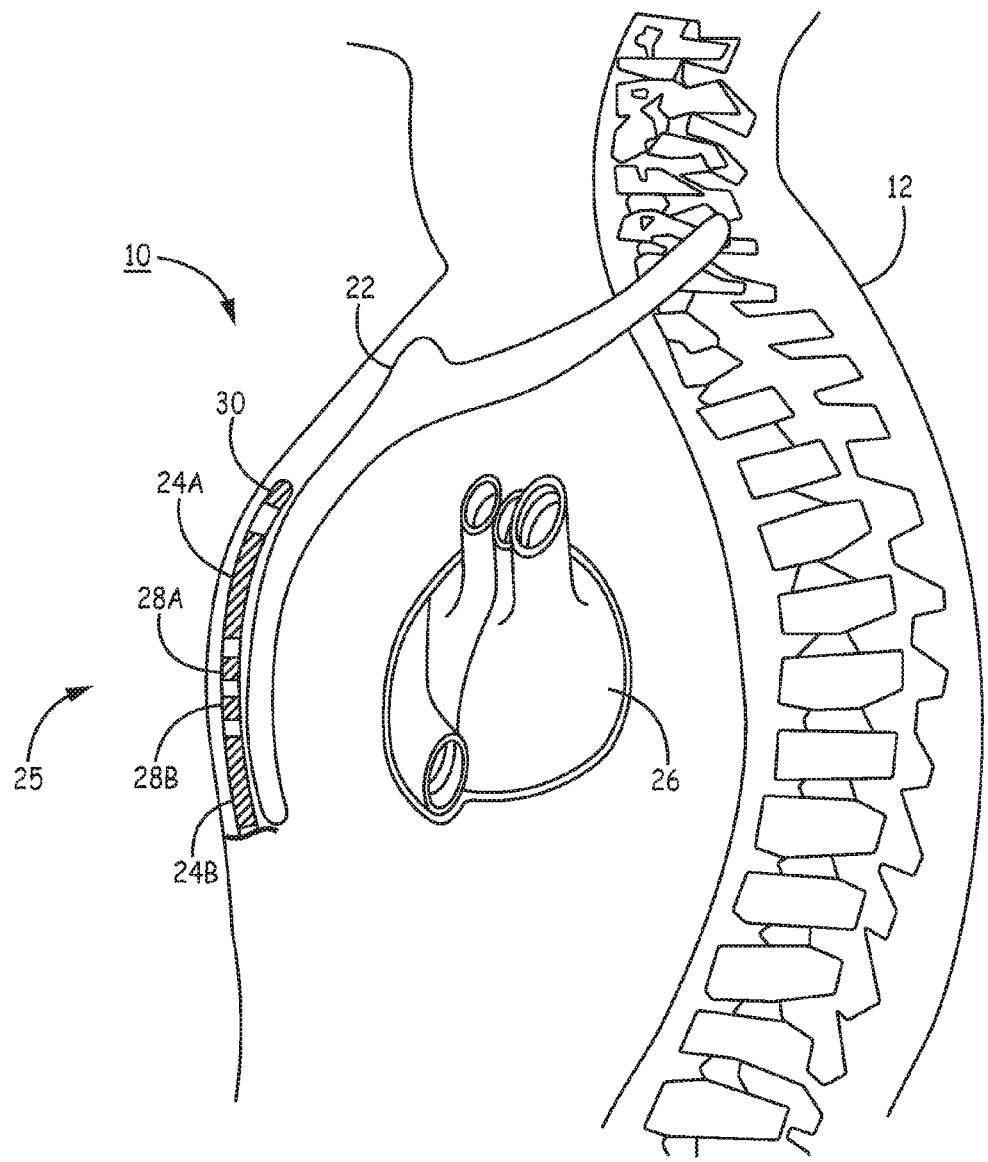

FIGS. 1A and 1B are conceptual diagrams of an extra-cardiovascular ICD system 10 according to one example. FIG. 1A is a front view of ICD system 10 implanted within patient 12. FIG. 1B is a side view of a portion of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a "can" electrode). In examples described herein, housing 15 may be used as an active can electrode for use in delivering cardioversion/defibrillation (CV/DF) shocks or other high voltage pulses delivered using a high voltage therapy module. In other examples, housing 15 may be available for use in delivering unipolar, cardiac pacing pulses in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within an elongated lead body 18 of lead 16 and electronic components included within the housing 15 of ICD 14. As will be described in further detail herein, housing 15 may house one or more processors, memories, transceivers, sensors, electrical sensing circuitry, therapy delivery circuitry, power sources and other appropriate components.

Elongated lead body 18 includes a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24A and 24B, collectively 24, and sense electrodes 28A, 28B, and 30. In some cases, defibrillation electrodes 24A and 24B may together form a defibrillation electrode in that they are configured to be activated concurrently. Alternatively, defibrillation electrodes 24A and 24B may form separate defibrillation electrodes in which case each of the electrodes 24A and 24B may be activated independently. In some instances, defibrillation electrodes 24A and 24B are coupled to electrically isolated conductors, and ICD 14 may include switching mechanisms to allow electrodes 24A and 24B to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24A and 24B (and in some example housing 15) may be referred to as defibrillation electrodes in some instances because they may be utilized, individually or collectively, for delivering high voltage stimulation therapy (e.g., cardioversion or defibrillation shocks). Electrodes 24A and 24B may be elongated coil electrodes and generally have a relatively high surface area for delivering high voltage electrical stimulation pulses compared to low voltage signals associated with sense electrodes 28A, 28B, and 30. However, electrodes 24A and 24B and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24A and 24B to use in only high voltage cardioversion/defibrillation therapy applications. As described herein, electrodes 24A and/or 24B may be used in a pacing electrode vector for delivering extra-cardiovascular pacing pulses using a high-voltage therapy circuitry of ICD 14.

Electrodes 28A, 28B and 30 are relatively smaller surface area electrodes for sensing cardiac electrical signals. Electrodes 28A, 28B and 30 are referred to as sense electrodes because they are generally configured for use in low voltage applications, e.g., used as either a cathode or anode for sensing of cardiac electrical signals. In some instances, electrodes 28A, 28B, and 30 may provide pacing functionality in addition to or instead of providing sensing functionality.

In the example illustrated in FIGS. 1A and 1B, electrodes 28A and 28B are located between defibrillation electrodes 24A and 24B and electrode 30 is located distal to defibrillation electrode segment 24A. Electrodes 28A and 28B are illustrated as ring electrodes, and electrode 30 is illustrated as a hemispherical tip electrode in the example of FIGS. 1A and 1B. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion 25 of lead 16. Further, electrodes 28A, 28B, and 30 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14 or other factors.

Electrical conductors (not illustrated) extend through one or more lumens of the elongated lead body 18 of lead 16 from the lead connector at the proximal lead end 27 to electrodes 24A, 24B, 28A, 28B, and 30 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24A and 24B and sense electrodes 28A, 28B, and 30. The respective conductors electrically couple the electrodes 24A, 24B, 28A, 28B and 30 to circuitry, such as a therapy module and/or a sensing module, of ICD 14 via connections in the connector assembly 17, including associated electrical feedthroughs crossing housing 15. The electrical conductors transmit therapy from a therapy module within ICD 14 to one or more of defibrillation electrodes 24A and 24B and/or electrodes 28A, 28B, and 30 and transmit sensed electrical signals from one or more of defibrillation electrodes 24A and 24B and/or sense electrodes 28A, 28B, and 30 to the sensing module within ICD 14.

FIGS. 1A and 1B are illustrative in nature and should not be considered limiting of the practice of the techniques disclosed herein. In other examples, lead 16 may include less than three sense electrodes or more than sense electrodes and/or a single defibrillation electrode or more than two electrically isolated or electrically coupled defibrillation electrodes or electrode segments. The sense electrodes 28A, 28B, and 30 may be located elsewhere along the length of lead 16, e.g., distal to defibrillation electrode 24A, proximal to defibrillation electrode 24B, and/or between electrodes 24A and 24B. For example, lead 16 may include a single sense electrode 28 between defibrillation electrodes 24A and 24B and no sense electrode distal to defibrillation electrode 24A or proximal to defibrillation electrode 24B.

In other examples, lead 16 may include only a single sense electrode 28 between defibrillation electrodes 24A and 24B and include another discrete electrode(s) distal to defibrillation electrode 24A and/or proximal to defibrillation electrode segment 24B. Various example configurations of extra-cardiovascular leads and electrodes and dimensions that may be implemented in conjunction with the extra-cardiovascular pacing techniques disclosed herein are described in commonly-assigned U.S. Pat. Publication No. 2015/0306375 (Marshall, et al.) and U.S. Pat. Publication No. 2015/0306410 (Marshall, et al.), both of which are incorporated herein by reference in their entirety.

In still other examples, ICD system 10 of FIGS. 1A and 1B may include a second extra-cardiovascular electrical stimulation and sensing lead similar to lead 16. The second lead may, for example, extend laterally to the posterior of patient 12 and include one or more electrodes that form an electrode vector with one or more of electrodes 24A, 24B, 28A, 28B, and/or 30 of lead 16 for providing pacing in accordance with the techniques disclosed herein.

In some instances, electrodes 24A, 24B, 28A, 28B, and/or 30 of lead 16 may be shaped, oriented, designed or otherwise configured to reduce extra-cardiac stimulation. For example, electrodes 24A, 24B, 28A, 28B, and/or 30 of lead 16 may be shaped, oriented, designed, partially insulated or otherwise configured to focus, direct or point electrodes 24A, 24B, 28A, 28B, and/or 30 toward heart 26. In this manner, electrical stimulation pulses delivered via lead 16 are directed toward heart 26 and not outward toward skeletal muscle. For example, electrodes 24A, 24B, 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When ICD 14 delivers pacing pulses via electrodes 24A, 24B, 28A, 28B, and/or 30, recruitment of surrounding skeletal muscle by the pacing pulses, which can cause discomfort to the patient, may be reduced by shaping, orienting, or partially insulating electrodes 24 to focus or direct electrical energy toward heart 26.

ICD 14 may obtain electrical signals corresponding to electrical activity of heart 26 via a combination of sensing vectors that include combinations of electrodes 28A, 28B, and 30 and the housing 15 of ICD 14. For example, ICD 14 may obtain cardiac electrical signals sensed using a sensing vector between combinations of electrodes 28A, 28B, and 30 with one another or obtain cardiac electrical signals using a sensing vector between any one or more of electrodes 28A, 28B, and 30 and the conductive housing 15 of ICD 14. In some instances, ICD 14 may even obtain cardiac electrical signals using a sensing vector that includes one or both defibrillation electrodes 24A or 24B such as between each other or in combination with one or more of electrodes 28A, 28B, and 30, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver one or more cardioversion or defibrillation shocks via one or both of defibrillation electrodes 24A and 24B and/or housing 15. ICD 14 may deliver the cardioversion or defibrillation shocks using electrodes 24A and 24B individually or together as a cathode (or anode) and with the housing 15 as an anode (or cathode).

ICD 14 also generate and deliver electrical stimulation pulses other than cardioversion or defibrillation shocks, including bradycardia pacing pulses, anti-tachycardia pacing (ATP) pulses, pacing pulses during asystole due to atrioventricular conduction block or post-shock, burst delivery for VF induction, and/or entrainment pacing pulses before a T-shock for VF induction. ICD 14 may deliver any or all of these pacing therapies using a therapy vector formed from electrodes 24A, 24B, and/or the housing 15. In one example, ICD 14 may deliver the pacing pulses using a pacing vector in which electrode 24A serves as an cathode (or anode) and electrode 24B serves as the anode (or cathode). ICD 14 may alternatively deliver the pacing pulses using electrodes 24A and 24B individually or together as a cathode (or anode) and with the housing 15 as an anode (or cathode). In some instances, ICD may also utilize one or more of 28A, 28B and/or 30 as part of the pacing vector.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver cardiac electrical stimulation pulses according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. For example, pacing capture threshold tests may be initiated by a user interacting with external device 40. A user may observe cardiac electrical signals retrieved from ICD 14 on a display of external device 40 for confirming cardiac capture by pacing pulses delivered by ICD 14 during a capture threshold test. External device 40 may alternatively be embodied as a home monitor or hand held device.

Figure 2A:
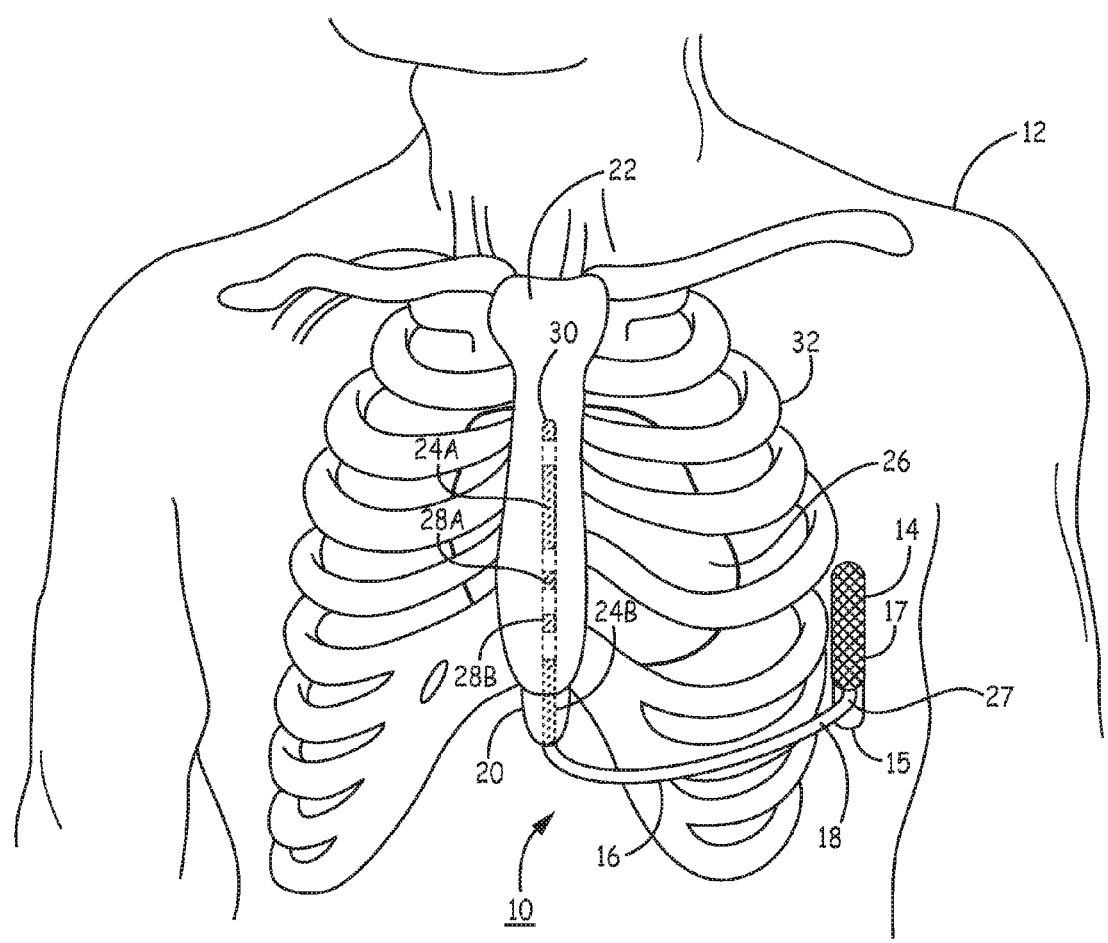
FIGS. 2A-2C are conceptual diagrams of a patient implanted with the extra-cardiovascular ICD system of FIG. 1A in a different implant configuration.
Figure 2B:
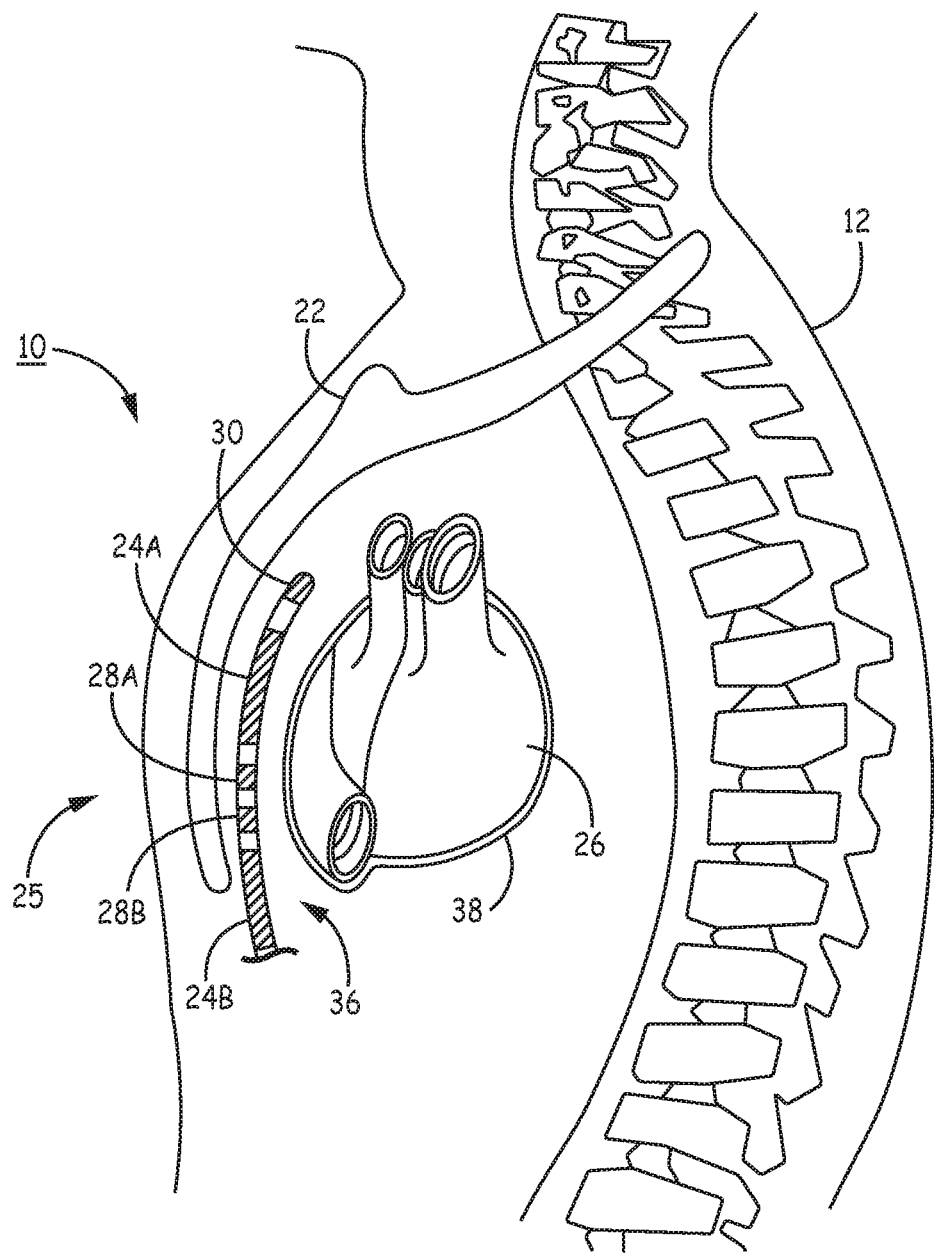
Figure 2C:
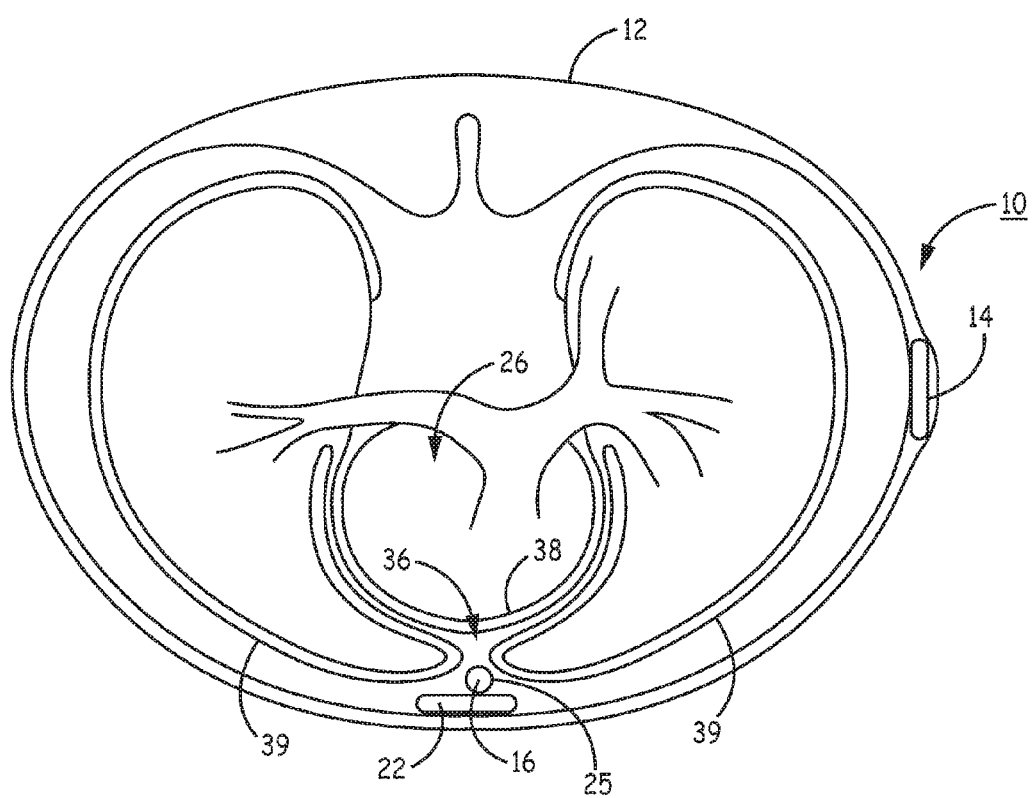

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 26. Other implant locations and lead and electrode arrangements that may be used in conjunction with the cardiac pacing techniques described herein are generally disclosed in the above-incorporated references. Although example extra-cardiovascular locations are described above with respect to FIGS. 1A, 1B and 2A-2C, the pacing techniques of this disclosure may be utilized in other implementations in which pacing amplitudes and/or widths associated with conventional intra-cardiac pacing pulses are insufficient to capture the patient's heart, including within the pericardial space.

Figure 3:
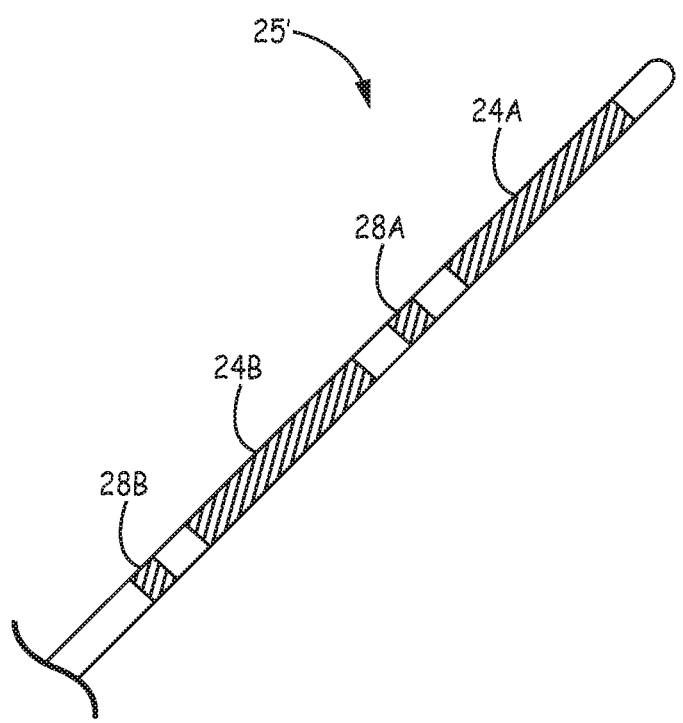
FIG. 3 is a conceptual diagram of a distal portion of an extra-cardiovascular lead having an electrode configuration according to another example.

FIG. 3 is a conceptual diagram illustrating a distal portion 25' of another example of implantable electrical lead 16 having an alternative electrode arrangement. In this example, distal portion 25' includes two sense electrodes 28A and 28B and two defibrillation electrodes 24A and 24B and respective conductors (not shown) to provide the electrical stimulation and sensing functionality as described above in conjunction with FIGS. 1A, 1B and FIGS. 2A-2C.

In this example, however, electrode 28B is proximal to proximal defibrillation electrode 24B, and electrode 28A is distal to proximal defibrillation electrode 24B such that electrodes 28A and 28B are separated by defibrillation electrode 24B. In a further example, in addition to electrodes 28A and 28B, lead 16 may include a third pace/sense electrode located distal to defibrillation electrode 24A.

The spacing and location of sense electrodes 28A and 28B may be selected to provide pacing vectors that enable efficient pacing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 3) may be less than or equal to 15 cm and may be less than or equal to 13 cm and or even less than or equal to 10 cm. The spacing and location of sense electrodes 28A and 28B may be selected to provide sensing vectors that enable efficient monitoring of the electrical activity of the heart 26. It is contemplated that one or more sense electrodes may be distal to distal defibrillation electrode 24A, one or more sense electrodes may be between defibrillation electrodes 24A and 24B, and/or one or more sense electrodes may be proximal to proximal defibrillation electrode 24B. Having multiple sense electrodes at different locations along lead body 18 enables selection from among a variety of inter-electrode spacings, which allows a sensing electrode vectors (e.g., pair or combinations) to be selected having an inter-electrode spacing that results in the greatest pacing efficiency.

Figure 4:
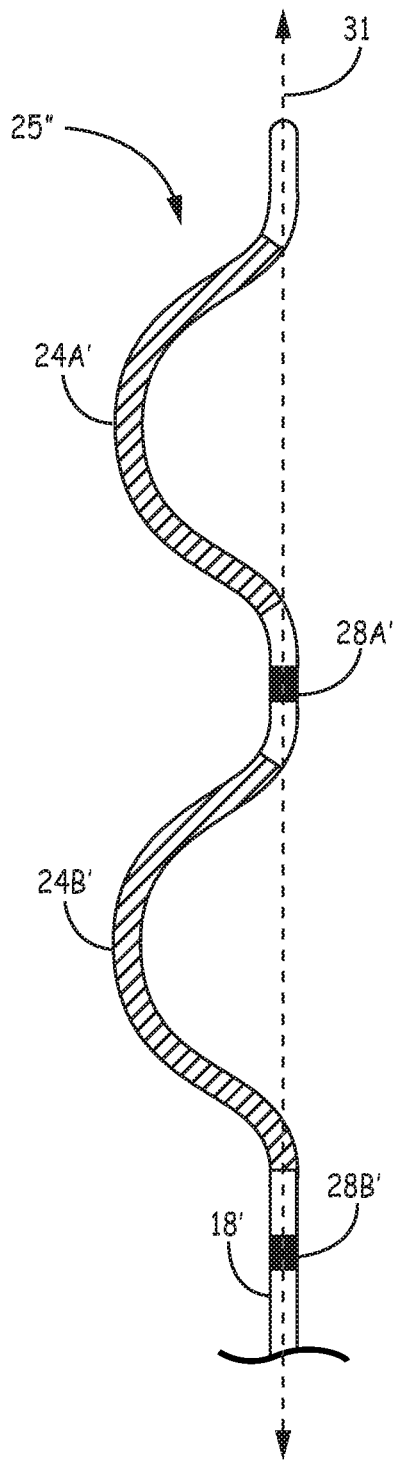
FIG. 4 is a conceptual diagram of a distal portion of an extra-cardiovascular lead having a lead body shape according to another example.

FIG. 4 is a conceptual diagram illustrating a distal portion 25" of another example of extra-cardiovascular lead 16 having an electrode arrangement similar to that of FIG. 3 but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along pre-formed curving portions of the lead body 18'. Sense electrode 28A' is carried between defibrillation electrodes 24A' and 24B'. Sense electrode 28B' is carried proximal to the proximal defibrillation electrode 24B'.

In one example, lead body 18' may be formed having a normally curving distal portion 25" that includes two "C" shaped curves, which together may resemble the Greek letter epsilon, "ε." Defibrillation electrodes 24A' and 24B' are each carried by the two respective C-shaped portions of the lead body distal portion 25" and extend or curve in the same direction. In the example shown, sense electrode 28A' is proximal to the C-shaped portion carrying electrode 24A', and sense electrode 28B' is proximal to the C-shaped portion carrying electrode 24B'. Sense electrodes 24A' and 24B' are approximately aligned with a central axis 31 of the normally straight or linear, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by curving serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 5:
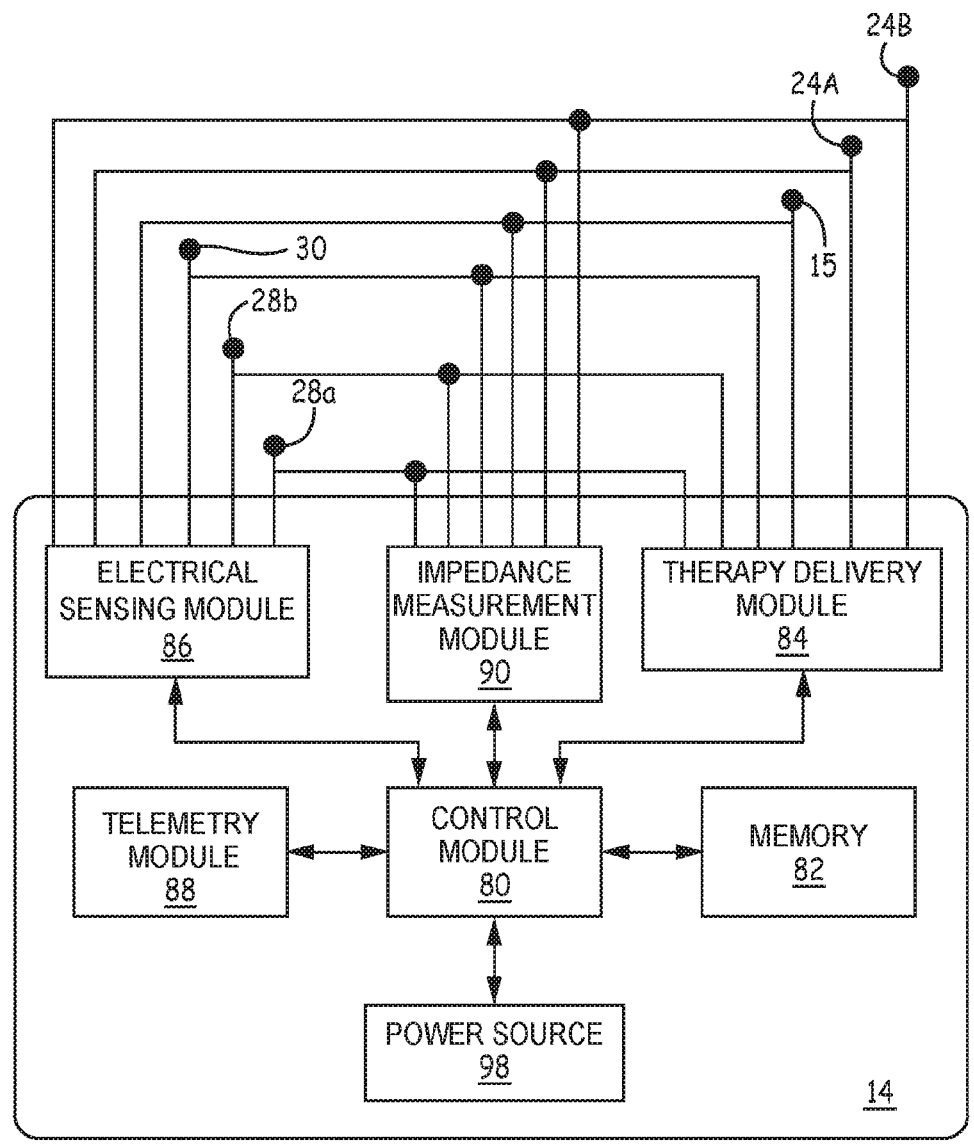
FIG. 5 is a schematic diagram of the ICD of the system of FIGS. 1A-2C according to one example.

FIG. 5 is a schematic diagram of ICD 14 according to one example. The electronic circuitry enclosed within housing 15 (shown schematically as a can electrode in FIG. 5) includes software, firmware and hardware that cooperatively monitor one or more cardiac electrical signals, determine when a pacing therapy is necessary, and deliver prescribed pacing therapies as needed. The software, firmware and hardware are also configured to determine when a CV/DF shock is necessary, and deliver prescribed CV/DF shock therapies. ICD 14 is coupled to an extra-cardiovascular lead, such as lead 16 carrying extra-cardiovascular electrodes 24A, 24B, 28A, 28B and 30, for delivering pacing therapies, CV/DF shock therapies and sensing cardiac electrical signals.

ICD 14 includes a control module 80, memory 82, therapy delivery module 84, electrical sensing module 86, and telemetry module 88. ICD 14 may include an impedance measurement module 90 for delivering a drive signal across a therapy delivery electrode vector and measuring a resulting voltage for determining an electrical impedance of the electrode vector.

A power source 98 provides power to the circuitry of ICD 14, including each of the modules 80, 82, 84, 86, 88, 90 as needed. Power source 98 may include one or more energy storage devices, such as one or more rechargeable or non-rechargeable batteries. The connections between power source 98 and each of the other modules 80, 82, 84, 86 and 88 are to be understood from the general block diagram of FIG. 5, but are not shown for the sake of clarity. For example, power source 98 is coupled to low voltage (LV) and high voltage (HV) charging circuits included in therapy delivery module 84 for charging LV and HV capacitors, respectively, or other energy storage devices included in therapy delivery module 84 for producing electrical stimulation pulses.

The functional blocks shown in FIG. 5 represent functionality included in ICD 14 and may include any discrete and/or integrated electronic circuit components that implement analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14 or those ICD modules. The non-transitory computer-readable media storing the instructions may include any of the media listed above.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware, firmware or software components, or integrated within common hardware, firmware or software components. For example, cardiac pacing operations may be performed by therapy delivery module 84 under the control of control module 80 and may include operations implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 may be electrically coupled to some or all of electrodes 24A, 24B, 28A, 28B, and 30 carried by lead 16 (shown in FIGS. 1A and 1B) and the housing 15, which may function as a common or ground electrode or as an active can electrode for delivering electrical stimulation therapy and/or sensing electrical signals.

Electrical sensing module 86 may be selectively coupled to electrodes 28A, 28B, 30 and housing 15 in order to monitor electrical activity of the patient's heart. Electrical sensing module 86 may additionally be selectively coupled to electrodes 24A and/or 24B. Sensing module 86 is enabled to selectively monitor one or more sensing vectors selected from the available electrodes 24A, 24B, 28A, 28B, 30 and housing 15. For example, sensing module 86 may include switching circuitry for selecting which of electrodes 24A, 24B, 28A, 28B, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A, 28B, 30 and housing 15. Each sensing channel may be configured to amplify, filter and rectify the cardiac electrical signal received from selected electrodes coupled to the respective sensing channel to improve the signal quality for sensing cardiac events, e.g., P-waves and/or R-waves. Each sensing channel includes cardiac event detection circuitry for sensing cardiac events from the received cardiac electrical signal developed across the selected sensing electrode vector(s). For example, each sensing channel in sensing module 86 may include an input or pre-filter and amplifier for receiving a cardiac electrical signal from a respective sensing vector, an analog-to-digital converter, a post-amplifier and filter, a rectifier to produce a digitized, rectified and amplified cardiac electrical signal that is passed to a cardiac event detector included in sensing module 86 and/or to control module 80. The cardiac event detector may include a sense amplifier, comparator or other circuitry for comparing the rectified cardiac electrical signal to a cardiac event sensing threshold, such as an R-wave sensing threshold, which may be an auto-adjusting threshold. Sensing module 84 may produce a sensed cardiac event signal in response to a sensing threshold crossing. The sensed cardiac events, e.g., R-waves, are used for detecting cardiac rhythms and determining a need for therapy by control module 80. In some examples, cardiac electrical signals such as sensed R-waves are used to detect capture of a pacing pulse delivered by ICD 14.

Therapy delivery module 84 includes includes high-voltage (HV) circuitry capable of delivering energy large enough to cardiovert/defibrillate a patient's heart. The HV circuitry of therapy delivery module 84 includes one or more high voltage capacitors. When a shockable rhythm is detected by ICD 14, the HV capacitor(s) is(are) charged by a HV charging circuit to a voltage level according to a programmed shock energy. The HV charging circuit may include a transformer and be a processor-controlled charging circuit that is controlled by control module 80. Control module 80 applies a signal to trigger discharge of the HV capacitor(s) upon detecting a feedback signal from therapy delivery module 84 that the HV capacitors have reached the voltage required to deliver the programmed shock energy. In this way, control module 80 controls operation of the high voltage circuitry of therapy delivery module 84 to deliver CV/DF shocks, e.g., using defibrillation electrodes 24A, 24B and/or housing 15.

Therapy delivery module 84 may be used to deliver cardiac pacing pulses when pacing pulses in addition to the high-voltage CV/DF shocks. In this case, the HV capacitor(s) is(are) charged to a much lower voltage than that used for delivering shock therapies. For example, the HV capacitor may be charged to 40 V or less, 30 V or less, or 20 V or less for producing extra-cardiovascular pacing pulses. In most instances, the HV circuitry is generally designed for delivery of the high-voltage CV/DF shocks which are typically associated with voltages that are much higher than the 40 V, 30V, or 20V. For example, the voltages associated with CV/DF shocks may be at least ten times greater than those voltages. The HV circuitry of therapy delivery module 84 may only be capable of producing reduced level voltages to a certain minimum level. The minimum level may be 10V in one example. In other examples the minimum voltage level may be 15V or even 20V depending on the design.

Compared to low-voltage pacing circuit outputs, therapy delivery module 84 may generate and deliver pacing pulses having a longer pulse width using the HV circuitry while still maintaining a pulse voltage amplitude that is greater than the pacing capture threshold when discharging the HV capacitor(s). The longer pulse width is attainable due to a higher capacitance (and consequently higher RC time constant) of the HV capacitor(s). The therapy delivery module 84 may be capable of producing a pulse voltage amplitude of at least the minimum voltage level attainable by the HV circuitry (e.g., 10 V or more, 15 V or more, 20 V or more). The therapy delivery module 84 may also produce mono- or multi-phasic pulses having a relatively longer pacing pulse width, e.g., 10 ms or more, because of the higher capacitance of high voltage capacitors included in HV circuitry. A typical HV pacing pulse width may be 10 ms; however an example range of available pulse widths may be 2 ms to 20 ms. Although capable of producing much higher voltage outputs, therapy delivery module 84 may cap the maximum voltage amplitude for delivering pacing pulses to avoid providing pulses that would be above a tolerable pain threshold of a patient. An example of a maximum voltage amplitude that may be used for delivering high voltage pacing pulses may be 40 V. However, the maximum voltage amplitude may be programmable and patient dependent. When a relatively higher pacing pulse voltage amplitude is tolerable by the patient, e.g., more than 10 V, a relatively shorter pacing pulse width, e.g., 2 to 5 ms, may be used during the high-voltage pacing output configuration. However, a longer pacing pulse width may be used as needed, e.g., a 10 V, 20 ms pacing pulse.

For the sake of comparison, the HV capacitor(s) of the therapy delivery module 84 may be charged to an effective voltage greater than 100 V for delivering a cardioversion/defibrillation shock. For example, two or three HV capacitors may be provided in series having an effective capacitance of 148 microfarads in therapy delivery module 84. These series capacitors may be charged to develop 750 to 800 V for the series combination in order to deliver shocks having a pulse energy of 5 Joules or more, and more typically 20 Joules or more. In ICDs implanted in extravascular locations, these pulse energies may be greater than 30 Joules and, in some instances, up to 80 Joules. The pacing pulses delivered by the therapy delivery module 84 will have a pulse energy in the milliJoule range or at least tenths of milliJoules. For instance, a pacing pulse generated by therapy delivery module 84 having a 10 V amplitude and 20 ms pulse width may be in the range of 2 to 5 milliJoules when the pacing electrode vector impedance is in the range of 400 to 1000 ohms. In contrast, pacing pulses delivered using endocardial electrodes or epicardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms.

As will be described below, control module 80 may enable a pacing using the high voltage circuitry of therapy delivery module 84 by applying at least a minimum electrical current required to enable switching circuitry included in HV circuitry for coupling the HV capacitor(s) to a pacing electrode vector. HV circuitry included in therapy delivery module 84 is described in further detail in conjunction with FIG. 8.

In some instances, control module 80 may control impedance measurement module 90 to determine the impedance of a pacing electrode vector. Impedance measurement module 90 may be electrically coupled to some or all of the available electrodes 24A, 24B, 28A, 28B, 30 and housing 15 for performing impedance measurements of one or more candidate pacing electrode vectors. Control module 80 may control impedance measurement module 90 to perform impedance measurements by passing a signal to impedance measurement module 90 to initiate an impedance measurement of a pacing electrode vector. Impedance measurement module 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control module 80.

As described in conjunction with FIG. 9 below, control module 80 may use the impedance measurement to set a variable shunt resistance included in HV circuitry of therapy delivery module 84 when a pacing configuration is selected for delivering extra-cardiovascular pacing pulses to heart 26. The variable shunt resistance may be parallel to the pacing load and set to be equal to or less than the pacing load impedance to maintain electrical current through HV switching circuitry throughout the duration of a pacing pulse delivered by the therapy delivery module 84 thereby promoting an appropriate voltage signal across the pacing load for capturing the patient's heart 26.

In some instances, therapy deliver module 84 may also include a low voltage pacing circuitry for delivering low voltage pacing pulses using an extra-cardiovascular pacing electrode vector selected from electrodes 24A, 24B, 28A, 28B, 30 and 15. LV therapy module 85 may be configured to deliver pacing pulses at maximum voltage levels below those available off the HV circuitry, e.g., less than 15V in one example, less than 10V in another example, or less than 8 V in a further example. In other examples, the voltage levels of the LV circuitry and the HV circuitry may overlap some. One or more capacitors included in the LV therapy module are charged to a voltage according to a programmed pacing pulse amplitude by a LV charging circuit, which may include a state machine. At an appropriate time, the LV therapy module couples the capacitor(s) to a pacing electrode vector to deliver a pacing pulse to the heart 26. Control parameters utilized by control module 80 for detecting cardiac rhythms and delivering electrical stimulation therapies (pacing pulses and CV/DF shocks) and tachyarrhythmia induction pulses may be programmed into memory 82 via telemetry module 88. Telemetry module 88 includes a transceiver and antenna for communicating with external device 40 (shown in FIG. 1A) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

Figure 6:
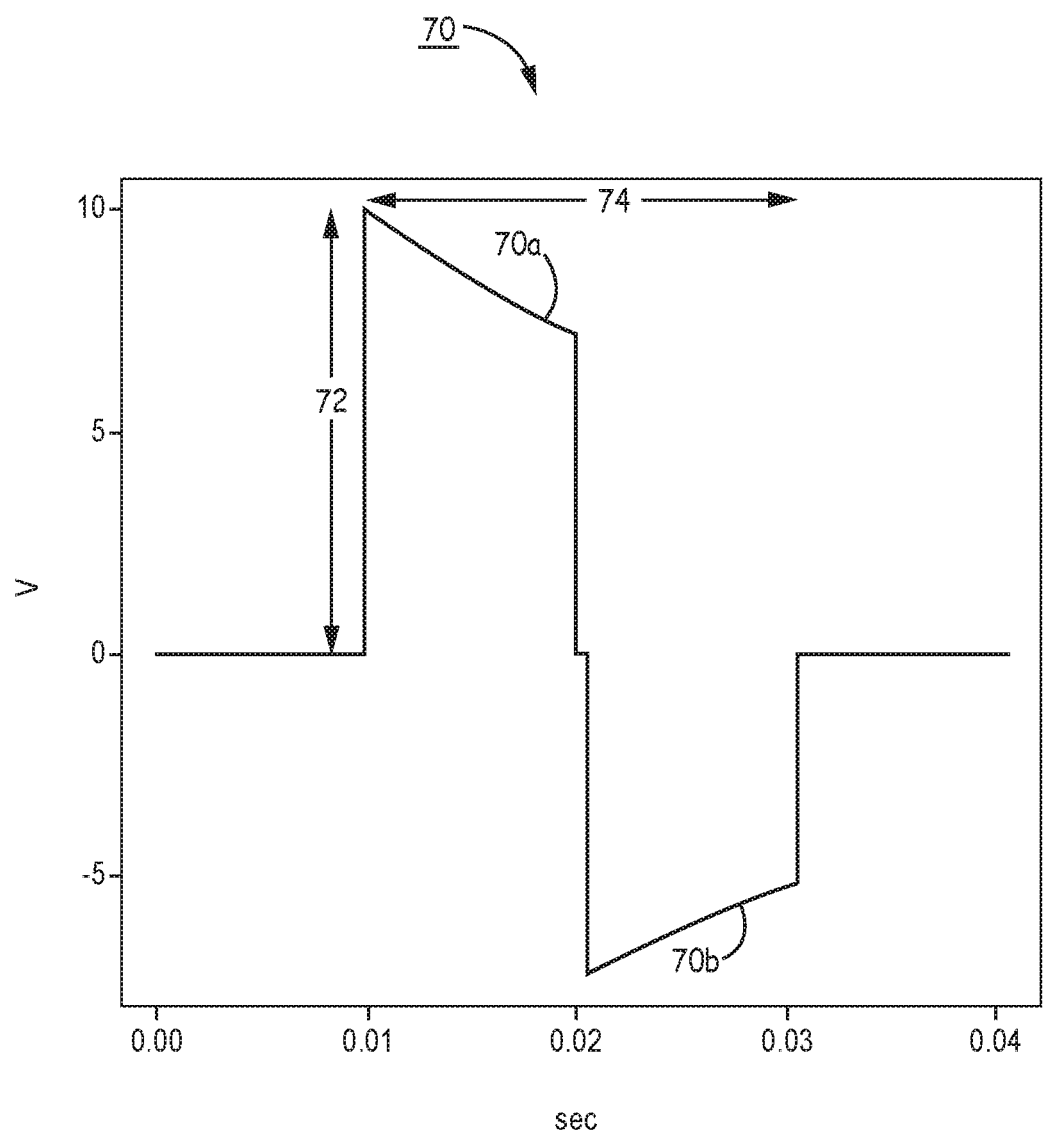
FIG. 6 is a depiction of one example of a high voltage pacing pulse that may be generated and delivered by the high voltage (HV) therapy module of the ICD of FIGS. 1A-2C to pace a patient's heart using extra-cardiovascular electrodes.

FIG. 6 is a depiction of one example of a high voltage pacing pulse 70 that may be generated and delivered by therapy delivery module 84 of ICD 14 to pace heart 26 using extra-cardiovascular electrodes when the HV circuitry is configured by control module 89 to a high-voltage pacing output configuration. Therapy delivery module 84 may produce high voltage pacing pulse 70 having a programmed pacing pulse amplitude 72 that is close to or greater than the maximum voltage amplitude that low voltage pacing circuits produce but is much less than the voltage amplitude of CV/DF shock pulses required to cardiovert or defibrillate the heart 26. As described above, the HV circuitry of therapy delivery module 84 may only be capable of producing voltages at a certain minimum level. The minimum level may be 10V in one example. In such a case, high voltage pacing pulse amplitude 72 may be greater than or equal to 10 V and up to a voltage that is tolerable to the patient, e.g., 20-40 V, e.g., greater than or equal to 10 V and up to 40 V, inclusive, or may be from 10 V to 30 V in other examples. In other examples the minimum voltage level may be higher or lower that 10 V, 15V or even 20V depending on the design. In another example, high voltage pacing pulse amplitude is greater than 8 V, up to and including 40 V. The high voltage pacing pulse 70 may have a pulse energy that is less than a defibrillation threshold of the heart 26. In the example shown, pacing pulse 70 has a pulse voltage amplitude of 10 V and a pulse width 74 of 20 ms. In another example, pacing pulse 70 has a pulse voltage amplitude equal to or between 10 and 20 V and a pulse width of 10 ms.

The pulse width 74 may depend on the pacing pulse amplitude 72 such that the total pacing pulse energy delivered by pulse 70 having amplitude 72 and width 74 successfully captures and paces heart 26, but may be less than a defibrillation threshold. In some examples, the pulse width 74 may be from 1 ms up to and including 10 ms, but may be shorter than or longer than this example range (e.g., up to 20 ms). The pulse width 74 may be set according to a pulse width threshold determined for the programmed pacing pulse amplitude 72. For example, if the pulse amplitude is set to a maximum setting tolerable to a patient (e.g., 20 V in on example), the minimum pulse width that successfully captures the heart may be determined during a pacing capture threshold test. Pacing pulse width 74 may be set at a safety pacing margin longer than the capture threshold pulse width. Alternatively, pulse width 74 may be set first and pulse amplitude 72 may be set to an amplitude that is a safety margin above the capture threshold pulse amplitude found during a pacing capture threshold test using the selected pulse width 74 when therapy delivery module 84 is enabled to deliver pacing pulses in a high-voltage pacing output configuration.

As shown, pacing pulse 70 is a biphasic pacing pulse having a first, positive-going portion 70a and a second, negative going portion 70b. A biphasic pacing pulse 70 may be produced by therapy delivery module 84 through the control of switching circuitry included in therapy delivery module 84. Switching circuitry of therapy delivery module 84 may controlled to reverse the polarity of the delivered pulse during capacitor discharging to produce the biphasic pulse. The polarity may be reversed at a given voltage threshold in some examples. The HV capacitor charged to the pulse voltage amplitude 72 continues to be discharged for the remaining portion 70b of pacing pulse width 74. As can be observed in FIG. 6, the ending voltage amplitude of the positive-going portion 70a is the starting voltage amplitude of the negative-going portion 70b because the same capacitor(s) continue to be discharged after switching circuitry reverses the polarity of the pacing pulse 70. In other examples, high voltage pacing pulse 70 may be delivered as a monophasic, other multi-phasic, or other shaped pulse through the control of the switching circuitry.

Figure 7:
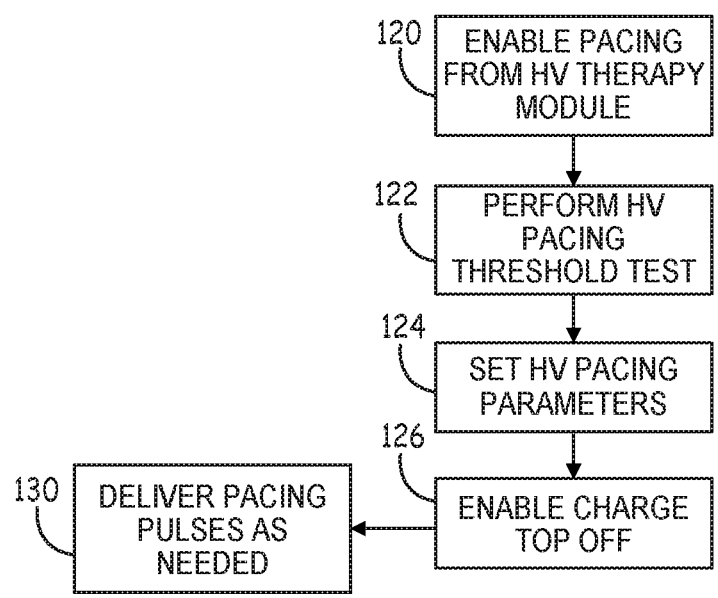
FIG. 7 is a flow chart of one method for selecting a pacing output configuration for use in delivering extra-cardiovascular cardiac pacing pulses by the ICD of FIGS. 1A-2C.

FIG. 7 is a flow chart 100 of one method for selecting a pacing output configuration for use in delivering extra-cardiovascular cardiac pacing pulses by ICD 14. FIG. 6 Control module 80 enables a high-voltage pacing configuration of therapy delivery module 84 at block 120. As described below with reference to FIG. 10, enabling the high-voltage pacing configuration by control module 80 may include setting a variable shunt resistance for delivering at least a minimum electrical current to switches included in the HV switching circuitry of therapy delivery module 84 to maintain desired switches in an active or closed state during a pacing pulse.

A capture threshold test may be performed at block 122 to determine appropriate high-voltage pacing control parameters. The capture threshold test may be performed by controlling therapy delivery module 84 to deliver one or more pacing pulses and determining whether capture occurred, automatically by control module 80 or manually by a user as described previously herein.

The HV therapy module 83 may be configured to deliver pacing pulses in the range of 10 V to 40 V, inclusive, in one example. The capture threshold test may be initiated by delivering a test pacing pulse having a pulse amplitude at or near the minimum pacing pulse amplitude available from therapy delivery module 84, e.g., 10 V in this example. The test pulse may also be delivered at a relatively narrow or minimum available pacing pulse width. In one example, the starting test pulse delivered during the capture threshold test at block 122 is a 10 V pulse having a 2 ms pulse width. If capture is achieved, the pacing control parameters for the high-voltage pacing output configuration are set at block 124.

If the starting test pulse does not capture the heart, control module 80 may control the therapy delivery module 84 to deliver test pacing pulses at higher voltage amplitudes and/or pulse widths. In one example, the threshold test for the high-voltage pacing configuration includes delivering pacing pulses having a minimum or default pulse width (e.g., 2 ms) at a starting pulse amplitude, which may be a minimum voltage amplitude the therapy delivery module 84 is capable of delivering (e.g., 10 V in this example). The control module 80 may then increase the voltage until a pulse amplitude capture threshold is identified up to a maximum of 40 V for the 2 ms pacing pulses. In another example, the threshold test for the high-voltage pacing configuration includes delivering pacing pulses having a minimum or default pulse width (e.g., 2 ms) at a starting pulse amplitude, which may be a minimum voltage amplitude the therapy delivery module 84 is capable of delivering (e.g., 10 V in this example). The control module 80 may then increase the pulse width until a maximum pulse width is reached (e.g., 20 ms) or capture threshold is identified. If no capture is detected for the maximum pulse width at the lowest pulse amplitude, then the control module 80 may increase the pulse amplitude a step and repeat the increase in pulse width and amplitude until capture is achieved.

The pacing control parameters set at block 124 may include some sort of safety margin to the parameters of the pulse that captured heart 26. For example, control module may set the pacing control parameters at block 124 to generate a pulse amplitude of 10 V and a pulse width of 10 ms when the 10 V, 2 ms pulse successfully captures heart 26. The leading edge voltage amplitude of the pacing pulse may cause pain or discomfort to the patient due to extra-cardiac capture of excitable tissue such as skeletal muscle. As such, the HV pacing control parameters may include a pacing pulse amplitude set to the minimum pulse amplitude that captures the patient's heart at a relatively short test pulse width, e.g., 2 ms, and a pacing pulse width that is set at to a relatively large safety margin greater than the test pulse width. The safety margin may be a fixed interval, e.g., 6 ms, 8 ms, 10 ms or other predetermined interval, greater than the test pulse width. Alternatively, the safety margin may be defined as a multiple of the test pulse width such as two times, three times, four times, five times, or other predetermined multiple. A maximum pulse width limit may be defined in some examples. In one example, the capture threshold test is performed at a pulse width of 2 ms, and a safety margin of 8 ms is added to the 2 ms test pulse width to set the high-voltage pacing pulse width at 10 ms. The leading edge voltage of the HV pacing pulses may not be increased above the capture threshold amplitude during pacing, but the large pulse width safety margin used in this case provides a high likelihood of successfully capturing the heart. Alternatively, an amplitude safety margin may be added to the pulse amplitude capture threshold to set the pacing pulse amplitude at block 124 in addition to setting the pacing pulse width to 10 ms, which may be a maximum available pacing pulse width for the high-voltage pacing output configuration. In other examples, longer pacing pulse widths may be available, but, for a given pacing pulse amplitude, the delivered energy of a pacing pulse that is longer than 10 ms may not increase significantly due to the decay rate of the pacing pulse. In yet another example, the pacing amplitudes and pulse widths that resulted in capture are set with no safety margins.

At block 126, control module 80 may enable top-off charging of a high voltage holding capacitor included in therapy delivery module 84 when the high-voltage pacing output configuration is selected based on the capture threshold testing. When pacing pulses are delivered in the high-voltage pacing configuration, the high voltage holding capacitor of HV therapy module 83 may be charged in anticipation of a required pacing therapy. Prior to a first pacing pulse, the charge on a high voltage holding capacitor, e.g., capacitor 210 of FIG. 8, may be topped off to the programmed pacing pulse voltage amplitude. For example, top-off charging may be enabled up to one second prior to delivering a pacing pulse, or upon anticipating a need for delivering a pacing pulse, which may be the first pacing pulse of a series of pulses delivered for capture threshold testing, ATP, post-shock pacing, bradycardia pacing or tachyarrhythmia induction. As such, therapy delivery module 84 may be enabled by control module 80 to perform capacitor charge top-off charging at times that a shock therapy may not be needed and in response to selecting the high voltage pacing configuration. In this way, delivery of the pacing pulse energy from the therapy delivery module 84 is readily available upon scheduling a pacing pulse.

After enabling the high-voltage pacing configuration and corresponding pacing control parameters (at blocks 106 and 108 or at blocks 114 and 116 or at blocks 120 and 124), ICD 14 delivers pacing pulses as needed according to programmed pacing therapies or tachyarrhythmia induction protocols at block 130. Bradycardia pacing pulses, ATP pulses, asystole pacing pulses post-shock or during atrioventricular conduction block, entrainment pulses prior to T-shock delivery for tachyarrhythmia induction, burst pulses for tachyarrhythmia induction, or other pacing therapies or tachyarrhythmia induction sequences may be delivered according to programmed pacing control parameters, including timing intervals such as ventricular lower rate intervals, atrio-ventricular pacing intervals, ATP inter-pulse intervals.

It is contemplated that in some examples, the pacing parameters set at block 124 may include enabling and/or disabling one or more pacing therapies. For example, if the high-voltage pacing configuration is enabled with a relatively high pacing amplitude that is tolerable for short intervals of time but intolerable by the patient for relatively longer periods of time, ATP therapy may be enabled which is of relatively short duration. Asystole pacing post-shock or during atrioventricular conduction block, which can be life-saving, may also (or alternatively) be enabled. Bradycardia pacing, which can be delivered over extended periods of time, may be disabled. As such, setting pacing parameters at block 124 by control module 80 may include enabling ATP therapy and/or asystole pacing and disabling bradycardia pacing. Asystole pacing may be provided when an R-wave is not sensed for an asystole back up pacing interval, e.g., 1.5 to 2 seconds. On the other hand, if pacing amplitudes of the pulses are configured to a level that is tolerable for the patient, bradycardia pacing and/or other pacing therapies that may extend over relatively long periods of time (e.g., minutes or hours) may be enabled at block 124, in addition to ATP and asystole pacing or other short duration or life-saving pacing therapies if the patient is highly tolerant of the extra-cardiovascular pacing pulses delivered.

It is recognized that in some patients reliable capture of heart 26 may still not be achieved even using the HV pacing configuration. Even if capture is achieved, a relatively high pacing capture threshold may exceed a tolerable level of pain caused by extra-cardiac capture of surrounding skeletal muscle. In this case, the HV pacing configuration may be disabled such that extra-cardiovascular pacing therapies are not delivered by ICD 14. In some cases, re-positioning of lead 16 and/or selection of a different pacing electrode vector may enable capture at a comfortable pacing output level.

Figure 8:
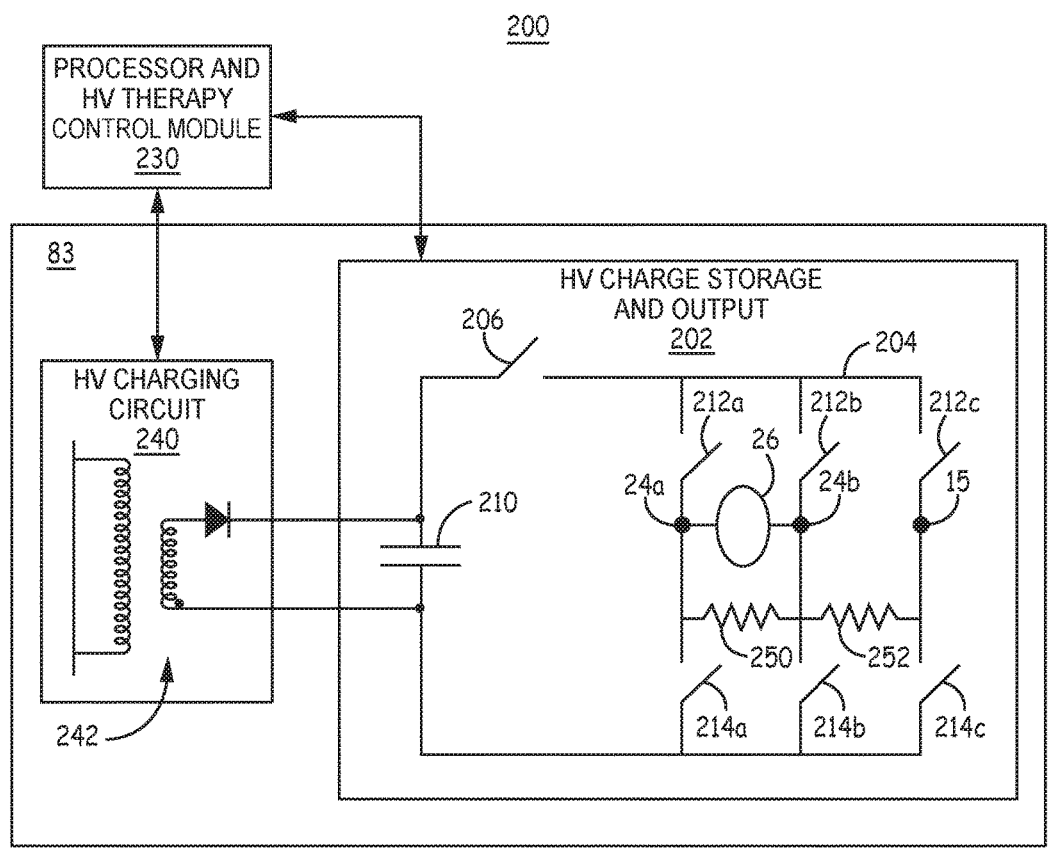
FIG. 8 is schematic diagram of a HV therapy module coupled to a processor and HV therapy control module of the ICD of FIGS. 1A-2C according to one example.

FIG. 8 is schematic diagram 200 of HV circuitry 83 of therapy delivery module 84 coupled to a processor and HV therapy control module 230. HV circuitry 83 includes a HV charging circuit 240 and a HV charge storage and output module 202. Processor and HV therapy control module 230 may be included in control module 80 for controlling HV charging circuit 240 and HV charge storage and output module 202. HV charge storage and output module 202 includes a HV capacitor 210 coupled to switching circuitry 204 via a pulse width control switch 206 for coupling the HV capacitor 210 to electrodes 24a, 24b and/or housing 15 to deliver a desired HV electrical stimulation pulse to the patient's heart 26. HV capacitor 210 is shown as a single capacitor, but it is recognized that a bank of two or more capacitors or other energy storage devices may be used to store energy for producing electrical signals delivered to heart 26. In one example, HV capacitor 210 is a series of three capacitors having an effective capacitance of 148 microfarads.

Switching circuitry 204 may be in the form of an H-bridge including switches 212a-212c and 214a-214c that are controlled by signals from processor and HV control module 230. Switches 212a-212c and 214a-214c may be implemented as silicon-controlled rectifiers (SCRs), insulated-gate bipolar transistors (IGBTs), metal-oxide-semiconductor field-effect transistors (MOSFETs), and/or other switching circuit components.

When control module 80 determines that delivery of an electrical stimulation pulse from HV circuitry 83 is needed, switching circuitry 204 is controlled by signals from processor and HV therapy control module 230 to electrically couple HV capacitor 210 to a therapy delivery vector to discharge capacitor 210 across the vector selected from electrodes 24a, 24b and/or housing 15. The selected electrodes 24a, 24b and/or housing 15 are coupled to HV capacitor 210 by opening (i.e., turning off or disabling) and closing (i.e., turning on or enabling) the appropriate switches of switching circuitry 204 to pass a desired electrical signal to the therapy delivery electrode vector. The electrical signal may be a monophasic, biphasic or other shaped CV/DF shock signal for terminating a ventricular tachyarrhythmia when VT or VF is detected.

For example, when a bi-phasic CV/DF shock is needed, one of switches 212a, 212b and 212c may be closed simultaneously with one of switches 214a, 214b and 214c without closing both of the "a," "b" or "c" switches across a given electrode 24a, 24b or housing 15, respectively, at the same time. To deliver a biphasic pulse using electrode 24a and housing 15, for instance, switch 212a and 214c may be closed to deliver a first phase of the biphasic pulse. Switches 212a and 214c are opened after the first phase, and switches 212c and 214a are closed to deliver the second phase of the biphasic pulse. Switches 212b and 214b remain open or disabled in this example with electrode 24b not selected or used in the therapy delivery vector. In other examples, electrode 24B may be included instead of electrode 24A or simultaneously activated with electrode 24A by closing switch 212b during the first phase and closing switch 214b in the second phase of the illustrative biphasic pulse.

When control module 80 enables the high-voltage pacing configuration, capacitor 210 is charged to a programmed pacing pulse amplitude by HV charging circuit under the control of processor and HV therapy control module 230. Switches 212a-212c and 214a-214c are controlled to be open or closed by processor and HV therapy control module 230 at the appropriate times for delivering a monophasic, biphasic or other desired pacing pulse by discharging capacitor 210 across the pacing load presented by heart 26 and a selected pacing electrode vector. The capacitor 210 is coupled across the selected pacing electrode vector for the programmed pacing pulse width.

In the example shown, the high-voltage pacing output configuration may be enabled using electrodes 24a and 24b carried by lead 16. Housing 15 may be unused by holding switches 212c and 214c open. Depending on the implant location of ICD 14 and lead 16 and the resulting electrical stimulation delivery vector between the housing 15 and one or both of electrodes 24a and 24b, greater recruitment of skeletal muscle may occur when housing 15 is included in the pacing electrode vector. A larger volume of skeletal muscle tissue may lie along a vector extending between the distal portion 25 of lead 16 and housing 15 than along a vector extending between the two electrodes 24a and 24b along lead distal portion 25. In the example configurations of FIGS. 1A-2C, for example, a pacing pulse may be delivered between the electrodes 24a and 24b to limit skeletal muscle recruitment compared to a pacing electrode vector that includes housing 15. In other electrode configurations and implant locations, the electrodes used to deliver extra-cardiovascular pacing pulses by HV circuitry 83 may be selected to provide a delivery vector that minimizes the volume of skeletal muscle included in the pacing electrode vector while directing sufficient energy to the heart 26 for capturing and pacing the heart.

A biphasic pacing pulse, such as pulse 70 of FIG. 6, may be delivered between electrodes 24a and 24b by producing a positive-going portion by closing switch 212a and switch 214b for a first portion 70a of pulse width 74 to discharge HV capacitor 210 across electrodes 24a and 24b through heart 26. The switches 212a and 214b are opened, and switches 212b and 214a are closed to deliver the negative-going phase, portion 70b, of the biphasic pacing pulse 70. All switches of switching circuitry 204 are opened upon expiration of the pulse width 74, e.g., based on a time out of a pulse width timer included in processor and HV therapy control module 230.

Between pacing pulses, as long as VT or VF are not being detected, the HV capacitor 210 is charged to the programmed pacing pulse amplitude. HV charging circuit 240 receives a voltage regulated signal from power source 98 (FIG. 5). HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV therapy control 230, which receives feedback signals from HV charge storage and output module 202 to determine when capacitor 210 is charged to a programmed voltage. A charge completion signal is passed to HV charging circuit 240 to terminate charging by processor and HV therapy control module 230. One example of a high voltage charging circuit and its operation is generally disclosed in U.S. Pat. No. 8,195,291 (Norton, et al.), incorporated herein by reference in its entirety.

While not shown in the example of FIG. 8, in other examples electrodes 28A, 28B and 30 may be selectively coupled to HV circuitry 83 via additional switches included in switching circuitry 204 so that HV pacing pulses may be delivered using a pacing electrode vector that includes electrodes 28A, 28B and/or 30.

HV charge storage and output module 202 is shown to include a shunt resistance 250 in parallel to the pacing load shown schematically as heart 26 when electrodes 24A and 24B are selected as the anode and cathode (or cathode and anode, respectively) of the pacing electrode vector. It is recognized that a shunt resistance may be provided in parallel to the pacing load for any selected pacing electrode vector, for example shunt resistance 252 is shown schematically if the pacing electrode vector includes electrode 24B and housing 15. Likewise a shunt resistance may be provided in parallel to the pacing load when the pacing electrode vector includes electrode 24A and housing 15.

Switches 212a-212c and switches 214a-214c may require a minimum current flow to hold them closed (i.e., ON or enabled) for passing current as capacitor 210 is discharged. This minimum current may be on the order of approximately 10 milliamps. Depending on the pacing load impedance and other conditions, the electrical current passing through enabled switches of switches 212a-212c and 214a-214c may fall below the minimum current required to keep the switches closed as capacitor 210 is discharged across a selected pacing vector. If the current passing through a respective switch falls below the minimum current required to keep the switch closed, the switch may open (or become disabled) causing premature truncation of the pacing pulse, which could result in loss of capture. As such, a minimum pacing pulse voltage amplitude may be set for the high-voltage pacing configuration in order to reduce the likelihood of the electrical current produced during capacitor discharge falling below the minimum current required to maintain a stable state of enabled switches of switching circuitry 204 during a programmed pacing pulse width.

The shunt resistance 250 or 252 may be a variable resistance that is set to match a pacing electrode vector impedance so that the load across heart 26 using a selected pacing electrode vector matches the shunt resistance. In this way, current through the switching circuitry 204 may be maintained at or above a minimum current required to maintain a stable state of enabled switches of switching circuitry 204 during the pacing pulse. If the shunt resistance 250 is higher than the pacing electrode vector impedance across heart 26, the electrical current applied to selected switches of switching circuitry 204 may fall below the minimum required to maintain the enabled state of the selected switches.

If the shunt resistance 250 or 252 is lower than the pacing electrode vector impedance, current produced by discharging capacitor 210 may be shunted away from the pacing load, e.g., the pacing electrode vector between electrodes 24a and 24b and heart 26, resulting in less energy delivered to heart 26, which may result in loss of capture. Accordingly, processor and HV therapy control module 230 may be configured to retrieve a pacing electrode vector impedance measurement from impedance measurement module 90 and set the shunt resistance 250 (or 252) to match the pacing electrode vector impedance.

In other examples, a minimum voltage charge of capacitor 210 may be set to provide the minimum current required to maintain an enabled state of selected switches of switching circuitry 204, but pacing energy may be intentionally shunted away from the pacing load including heart 26 in order to reduce the delivered pacing pulse energy. If the pacing amplitude capture threshold is below the minimum voltage amplitude required to maintain the minimum current to keep switches 212a-212c and 214a-214c on when they are enabled by processor and HV therapy control module 230, the energy delivered across the pacing electrode vector may be reduced by setting the variable shunt resistance 250 (or 252) to a value that is less than the pacing electrode vector impedance. This current shunting may reduce skeletal muscle recruitment caused by the extra-cardiovascular pacing pulse while still providing effective capture of heart 26.

Since the range of pacing load impedances and pacing voltage amplitudes may vary between patients and at different times within a patient, a variable shunt resistance may be provided to enable selection of the appropriate resistance for shunting the required current through the switching circuitry. It is contemplated, however, that in some examples a fixed resistance shunt may be provided. For example, the resistance needed to shunt current to the switching circuit when the pacing load impedance is high may still shunt some current to the switching circuitry when the pacing load impedance is relatively lower. An optimal value for a fixed resistance shunt may be determined based on empirical data, e.g., typical pacing load impedances and pacing pulse voltage amplitudes used clinically.

Figure 9:
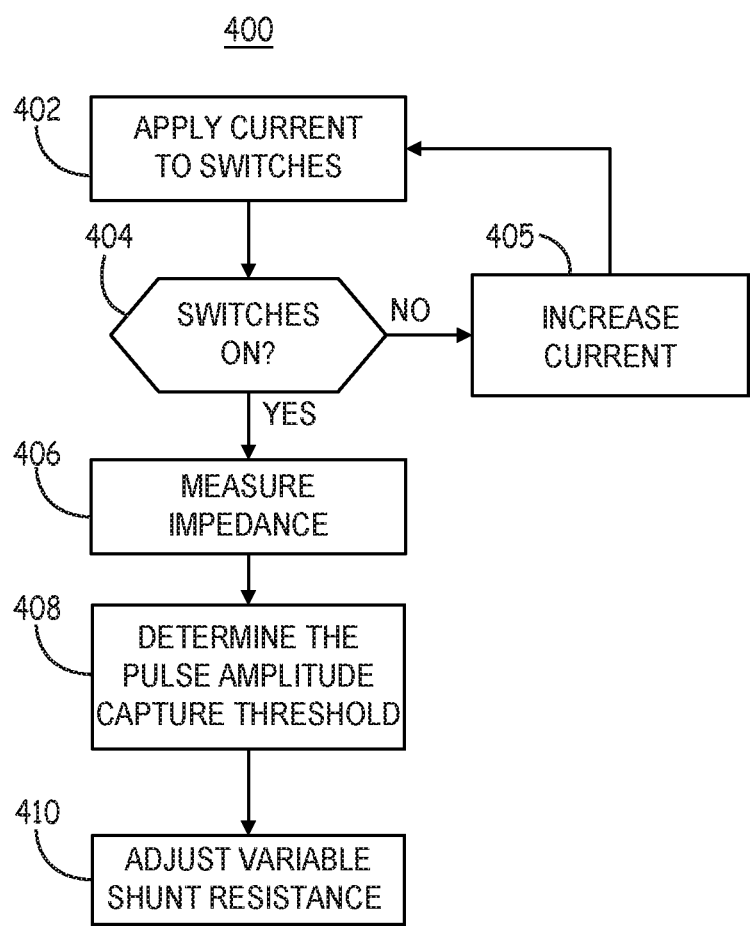
FIG. 9 is a flow chart of one method that may be performed by the ICD of FIGS. 1A-2C for enabling a high-voltage, pacing output configuration.

FIG. 9 is a flow chart 400 of one method that may be performed by ICD 14 as part of enabling a high-voltage, pacing output configuration at block 120 of FIG. 7. At block 402, processor and HV therapy control module 230 may control the HV circuitry 83 to apply electrical current to switching circuitry 204. Current is applied to selected ones of switches 212a-212c and 214a-214c in order enable or activate the selected switches to select a desired pacing electrode vector. A minimum electrical current is required in order to maintain an enabled switch of switching circuitry 204 in the ON or closed state. If the current is too low, the switch may open.

At block 404, processor and HV therapy control module 230 may receive a feedback signal from switching circuitry 204 indicating that the selected switches are ON or enabled. If the selected switches of switching circuitry 204 are not enabled by the current applied at block 402, the applied electrical current may be increased at block 405. The feedback signal may be a sampled electrical current signal or a sampled impedance signal in switching circuitry 204.

Once the desired switches are enabled, an impedance measurement may be made at block 406 by impedance measurement module 90 under the control of processor and HV therapy control module 230. In some examples, the variable shunt resistance 250 is adjusted to match the measured pacing electrode vector impedance at block 410. By setting the variable shunt resistance 250 to match the pacing load resistance, the enabled switches of switching circuitry 204 will remain enabled by the required minimum current when capacitor 210 is discharging across the pacing load. In another example, the electrical current on an output line to the pacing load from HV charge storage and output module 202 is sampled. If the sampled electrical current is zero, the shunt resistance 250 is decreased.

In other examples, the control module 80 may control high voltage therapy module 83 to perform a pacing amplitude threshold test at block 408. If the minimum charge voltage of capacitor 210 required to maintain a minimum electrical current applied to enable switches of switching circuitry 204 is greater than the pacing amplitude capture threshold, the variable shunt resistance 250 may be adjusted to a resistance that is less than the pacing load impedance. A shunt resistance that is lower than the pacing load resistance will shunt current away from the pacing load and thereby reduce energy delivered across the pacing electrode vector to the patient's heart. For example, a minimum 10 V charge of capacitor 210 may be required in order to apply and maintain the minimum electrical current needed to keep selected switches of switching circuitry 204 enabled. During a threshold test, if a pacing pulse having the minimum 10 V amplitude and a relatively short pulse width, e.g., 2 ms, captures the patient's heart 26, the pulse amplitude capture threshold may be less than 10 V and even more likely less than 10 V when a longer pulse width is used, e.g., 10 ms. A lower energy pacing pulse may be tested by decreasing the variable shunt resistance so that some pacing energy is shunted across shunt resistor 250 rather than across the pacing electrode vector. If capture still occurs, the pacing capture threshold is less than the minimum voltage charge of capacitor 210 that is required to produce the minimum current for enabling the switches 212a-212c and 214a-214c of circuitry 204.

If this is the case, the variable shunt resistance 250 may be adjusted at block 410 to a resistance that is less than the pacing electrode vector impedance to reduce the energy delivered to heart 26 (and surrounding skeletal muscle) when capacitor 210 is charged to the minimum voltage and discharged across the pacing load. If the pulse amplitude capture threshold is equal to or greater than the minimum charge voltage of capacitor 210, the variable shunt resistance may be set to match the pacing electrode vector impedance. As such, the variable shunt resistance 250 provided in parallel to the pacing electrode vector may be adjusted by processor and HV control module 230 based on the pacing electrode vector impedance (e.g., matching the pacing electrode vector impedance). In other examples, the variable shunt resistance 250 is set based on pacing electrode vector impedance and the pulse amplitude capture threshold. When the pulse amplitude capture threshold is equal to or greater than the minimum charge of capacitor 210 required to maintain a minimum required current to switches of switching circuitry 204, the variable shunt resistance 250 may be set to match the pacing electrode vector impedance. When the pulse amplitude capture threshold is less than the minimum required charge of capacitor 210, the variable shunt resistance 250 may be set to a value that is less than the pacing electrode vector impedance.

In some examples, some or all of the process shown by flow chart 400 including measuring impedance at block 406 and adjusting the variable shunt resistance based on the pacing electrode vector impedance at block 410 is performed for every pacing pulse delivered by ICD 14 when the high-voltage, pacing output configuration is enabled. In this way, the variable shunt resistance may be adjusted on a pulse-by-pulse basis to match (or in some cases be less than) the pacing load resistance for every pacing pulse and thereby minimize the likelihood of any of the switches of switching circuitry 204 being inadvertently disabled due to low current flow, which could result in a non-delivered or prematurely truncated pacing pulse and loss of capture.

Thus, a method and apparatus for delivering cardiac pacing pulses using an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An extra-cardiovascular implantable cardiac device comprising:
a high voltage therapy module including:
a high voltage capacitor;
a high voltage charging circuit configured to charge the high voltage capacitor;
switching circuitry configured to couple the high voltage capacitor across a pacing load that includes extra-cardiovascular electrodes; and
a variable shunt resistance in parallel with the pacing load; and
a control module coupled to the high voltage therapy module and configured to:
apply an electrical current to enable the switching circuitry;
set the variable shunt resistance to a value that keeps the switching circuitry enabled during delivery of one or more pacing pulses to the pacing load; and
control the high voltage therapy module to generate and deliver the one or more extra-cardiovascular pacing pulses via the extra-cardiovascular electrodes.

2. The cardiac device of claim 1, further comprising an impedance measurement module, wherein the control module is configured to:
control the impedance measurement module to measure an impedance of the pacing load that includes the extra-cardiovascular electrodes; and
set the variable shunt resistance to a value selected based on the measured impedance.

3. The cardiac device of claim 2, wherein the control module is configured to set the variable shunt resistance equal to the impedance.

4. The cardiac device of claim 2, wherein the control module is configured to set the variable shunt resistance less than the impedance.

5. The cardiac device of claim 2, wherein the control module is further configured to:
control the high voltage therapy module to perform a test to determine a pacing amplitude capture threshold;
determine if the pacing amplitude capture threshold is less than a minimum voltage charge of the high voltage capacitor required to produce the electrical current to enable the switching circuitry; and
set the variable shunt resistance to be less than the impedance in response to the pacing amplitude capture threshold being less than the minimum voltage charge.

6. The cardiac device of claim 2, wherein the control module is configured to control the impedance measurement module to measure an impedance of the pacing load that includes the extra-cardiovascular electrodes and set the variable shunt resistance to a value selected based on the measured impedance on a pulse-by-pulse basis.

7. The cardiac device of claim 1, wherein the control module is further configured to enable a first pacing therapy comprising extra-cardiovascular pacing pulses delivered using the high voltage therapy module and disabling a second pacing therapy comprising extra-cardiovascular pacing pulses from being delivered using the high voltage therapy module.

8. The cardiac device of claim 7, wherein the first pacing therapy comprises at least one of anti-tachycardia pacing (ATP) therapy and/or asystole pacing therapy and the second pacing therapy comprises bradycardia pacing therapy.

9. The cardiac device of claim 1, wherein the control module is further configured to enable top-off charging of the high voltage capacitor in response to applying the electrical current to enable the switching circuitry.

10. The cardiac device of claim 1, wherein the high voltage charging circuit further comprises a transformer for charging the high voltage capacitor.

11. The cardiac device of claim 1, wherein the control module is configured to control the high voltage therapy module to charge the high voltage capacitor to a first voltage to deliver the one or more pacing pulses and to charge the high voltage capacitor to a second voltage to deliver a defibrillation shock via the extra-cardiovascular electrodes, the second voltage being larger than the first voltage.

12. The cardiac device of claim 11, further comprising:
a housing enclosing the high voltage therapy module and the control module; and
an extra-cardiovascular lead couplable to the cardiac device and carrying at least a first extra-cardiovascular electrode and a second extra-cardiovascular electrode of the plurality of implantable extra-cardiovascular electrodes;
wherein the control module controls the high voltage therapy module to:
deliver the one or more pacing pulses via a first extra-cardiovascular electrode vector comprising the first extra-cardiovascular electrode carried by the extra-cardiovascular lead and the second extra-cardiovascular electrode carried by the extra-cardiovascular lead; and
deliver the defibrillation shock via a second extra-cardiovascular electrode vector including the housing and at least one of the first extra-cardiovascular electrode or the second extra-cardiovascular electrode carried by the extra-cardiovascular lead.

13. The cardiac device of claim 1, further comprising an extra-cardiovascular lead couplable to the cardiac device and carrying at least a pair of the extra-cardiovascular electrodes, wherein the control module is configured to control the switching circuitry to deliver the pacing pulses across the pair of extra-cardiovascular electrodes when the extra-cardiovascular lead is coupled to the cardiac device.

14. An extra-cardiovascular implantable cardiac device comprising:
a high voltage therapy module including:
a high voltage capacitor;
a high voltage charging circuit configured to charge the high voltage capacitor;
switching circuitry configured to couple the high voltage capacitor across a pacing load that includes extra-cardiovascular electrodes; and
a shunt resistance in parallel with the pacing load, wherein a value of the shunt resistance is selected to keep the switching circuitry enabled during delivery of one or more pacing pulses to the pacing load over desired range of pacing amplitudes and pacing load impedances; and
a control module coupled to the high voltage therapy module and configured to:
apply an electrical current to enable the switching circuitry; and
control the high voltage therapy module to generate and deliver the one or more extra-cardiovascular pacing pulses via the extra-cardiovascular electrodes.

15. An extra-cardiovascular implantable cardiac device comprising:
a high voltage therapy module including:
a high voltage capacitor;

a high voltage charging circuit configured to charge the high voltage capacitor;

switching circuitry configured to couple the high voltage capacitor across a pacing load that includes extra-cardiovascular electrodes; and a shunt resistance in parallel with the pacing load; and a control module coupled to the high voltage therapy module and configured to:

apply an electrical current to enable the switching circuitry;

select a pacing pulse voltage amplitude to have a minimum pacing pulse voltage amplitude to keep the switching circuitry enabled during delivery of one or more pacing pulses to the pacing load; and control the high voltage therapy module to generate and deliver the one or more extra-cardiovascular pacing pulses via the extra-cardiovascular electrodes.

16. A method performed by an extra-cardiovascular implantable cardiac device having a high voltage therapy module, the method comprising:

applying, by a control module of the cardiac device, an electrical current to enable switching circuitry configured to couple a high voltage capacitor of the therapy module across a pacing load that includes extra-cardiovascular electrodes;

setting, by the control module of the cardiac device, a variable shunt resistance of the therapy module, the variable shunt resistance being in parallel with the pacing load, to a value that keeps the switching circuitry enabled during delivery of one or more pacing pulses to the pacing load;

controlling the high voltage therapy module to charge a high voltage capacitor of the therapy module; and configuring the switching circuitry to discharge the high voltage capacitor across the pacing load to deliver the one or more pacing pulses via the extra-cardiovascular electrodes.

17. The method of claim 16, further comprising:

measuring an impedance of the pacing load that includes the extra-cardiovascular electrodes; and setting the variable shunt resistance to a value selected based on the measured impedance.

18. The method of claim 17, wherein setting the variable shunt resistance to a value selected based on the measured impedance comprises setting the variable shunt resistance equal to the impedance.

19. The method of claim 17, wherein setting the variable shunt resistance to a value selected based on the measured impedance comprises setting the variable shunt resistance to a value less than the impedance.

20. The method of claim 17, further comprising:

controlling the high voltage therapy module to perform a test to determine a pacing amplitude capture threshold;

determining if the pacing amplitude capture threshold is less than a minimum voltage charge of the high voltage capacitor required to produce the electrical current to enable the switching circuitry; and setting the variable shunt resistance to be less than the impedance in response to the pacing amplitude capture threshold being less than the minimum voltage charge.

21. The method of claim 17, wherein the measuring and setting are done on a pulse-by-pulse basis.

22. The method of claim 17, further comprising:

enabling a first pacing therapy including the one or more extra-cardiovascular pacing pulses generated by the high voltage therapy module; and disabling a second pacing therapy including the one or more extra-cardiovascular pacing pulses from being delivered using the high voltage therapy module.

23. The method of claim 22, wherein the first pacing therapy comprises at least one of anti-tachycardia pacing (ATP) therapy and/or asystole pacing therapy and the second pacing therapy comprises bradycardia pacing therapy.

24. The method of claim 17, further comprising enabling top-off charging of the high voltage capacitor in response to applying the electrical current to enable the switching circuitry.

25. The method of claim 17, wherein controlling the high voltage therapy module to charge a high voltage capacitor of the therapy module comprises controlling the high voltage therapy module to charge the high voltage capacitor using a transformer.

26. The method of claim 17, further comprising:

charging the high voltage capacitor to a first voltage to deliver the one or more pacing pulses; and charging the high voltage capacitor to a second voltage to deliver a defibrillation shock via the extra-cardiovascular electrodes, the second voltage being larger than the first voltage.

* * * * *